United States Patent [19]

Klein

[11] Patent Number: 5,599,546
[45] Date of Patent: Feb. 4, 1997

[54] MEDICINAL FACIAL MASK

[76] Inventor: Marvin E. Klein, 27629 Chatsworth, Farmington Hills, Mich. 48334

[21] Appl. No.: 109,720

[22] Filed: Aug. 19, 1993

Related U.S. Application Data

[63] Continuation-in-part of Ser. No. 64,915, May 24, 1993, abandoned, which is a continuation-in-part of Ser. No. 899,418, Jun. 16, 1992, abandoned.

[51] Int. Cl.$^6$ .............................. A61K 7/02; A61K 47/02
[52] U.S. Cl. .......................... 424/401; 424/69; 514/859; 514/974
[58] Field of Search ............ 424/401, 69; 514/844–848, 514/858–865, 827–828, 886–87, 974, 772.2, 781–82, 778–79, 774, 770; 524/447

[56] References Cited

U.S. PATENT DOCUMENTS

| | | | |
|---|---|---|---|
| 3,023,144 | 2/1962 | Greathouse | 167/58 |
| 3,879,537 | 4/1975 | Van Scott et al. | 424/311 |
| 3,984,566 | 10/1976 | Van Scott et al. | 424/283 |
| 3,988,470 | 10/1976 | Van Scott et al. | 424/283 |
| 4,021,572 | 5/1977 | Van Scott et al. | 424/317 |
| 4,105,783 | 8/1978 | Yu et al. | 424/283 |
| 4,126,142 | 11/1978 | Saute | 424/78.03 |
| 4,234,599 | 11/1980 | Van Scott et al. | 424/279 |
| 4,380,549 | 4/1983 | Van Scott et al. | 424/317 |
| 4,540,572 | 4/1985 | Seth | 514/887 |
| 4,640,932 | 2/1987 | Fong et al. | 514/714 |
| 4,775,530 | 10/1988 | Perricone | 424/73 |
| 5,073,573 | 12/1991 | Schanz et al. | 424/47 |
| 5,091,171 | 2/1992 | Yu et al. | 424/642 |

*Primary Examiner*—Edward J. Webman
*Attorney, Agent, or Firm*—Gifford, Krass, Groh, Sprinkle, Patmore, Anderson & Citkowski, P.C.

[57] ABSTRACT

A class of dermatological compositions and method of treating various skin conditions. The compositions includes an acidic material selected from the group consisting of alphahydroxy acids, carboxylic acids, halocarboxylic acids, dicarboxylic acids, and combinations thereof, a limonene-based oil, an absorbent carrier, and water. The compositions are applied to the skin as a facial mask and allowed to dry. The compositions both degrease the skin, and deliver therapeutic agents to the skin on a time release basis.

13 Claims, No Drawings

MEDICINAL FACIAL MASK

REFERENCE TO RELATED APPLICATION

This application is a continuation-in-part of application Ser. No. 064,915, filed May 24, 1993, now abandoned, which is a continuation-in-part of application Ser. No. 899,418, filed Jun. 16, 1992, now abandoned.

FIELD OF THE INVENTION

This invention relates to pharmaceutically and cosmetically-acceptable compositions and a method for the topical treatment of skin disorders such as dry skin, photo-aging, and folliculitis barbae employing the compositions.

BACKGROUND OF THE INVENTION

Conventional treatments of skin disorders typically involves the topical application to affected areas of hydrating emollient or moisturizer compositions including an active agent of choice, an example of which is an alphahydroxy acid (AHA) such as glycolic acid and the like. Compositions of this type are described in U.S. Pat. Nos. 3,879,537; 3,920,835; 3,920,840; 3,984,566; 3,988,470; 4,021,572; 4,104,782; 4,105,783; 4,197,316; 4,234,599; 4,246,261; 4,363,815; and 4,380,549.

In the treatment of certain skin conditions with such compositions which ordinarily have a pH of about 2 or less, it was found the compositions undesirably caused some skin irritation with redness and sensation of burning. One solution which was offered to avoid this problem was to lower the concentration of the hydroxy acid in the composition. Another solution was to partially or wholly neutralize the hydroxy acid with a base such as ammonium hydroxide, in order to raise the pH from below 2 to near pH 4. However, these neutralization methods make the product ineffective (see *Dermatology Times*, May 1992). Furthermore, the use of AHA as a skin treatment for such disorders as dry skin, dermatosis, acne, keratosis, photo-aging, melasma, itching, inflammation and facial or razor bumps requires a preliminary step of applying a degreaser to the skin to remove the skin oils therefrom. Applying prior art AHA compositions to the degreased skin has the further disadvantage of delivering the therapeutic agent rapidly, and often unevenly to the surface of the skin. Results from such treatment can be less than satisfactory.

Accordingly, there is need for acceptable AHA-based compositions and treatments which eliminate the need for the separate degreasing step. There is also a need for such compositions and treatments which deliver the therapeutic agent in a more uniform, time-controlled manner. The present invention contemplates novel pharmaceutically and cosmetically AHA and AHA-like compositions which may be used in a one-step process both to degrease and treat the skin, while at the same time providing for time release of the therapeutic agent.

SUMMARY OF THE INVENTION

The invention is a class of compositions which may be used as a facial mask for treating such skin conditions as dry skin, photo-aging and folliculitis barbae, and a method of using the compositions.

The invention, in its broadest aspect, is comprised of up to 20% of an acidic material selected from the group consisting of: alphahydroxy acids, carboxylic acids, halo-carboxylic acids, dicarboxylic acids, and combinations thereof; up to 50% of an absorbent carrier, and the balance water. The absorbent carrier may be any substance, or combination of substances, which is capable, when combined with the therapeutic agents and water, of forming a mud pack material which can then be applied to the skin of the user. Typical examples of suitable absorbent carriers include: mineral-based carriers such as kaolin and bentonite clays and veegum (magnesium aluminum silicate); cellulose-based materials such as starches, guar gums, cellulosic gums, alginates, pulpates, and solulan 98 (methylcellulose); polymeric materials such as polyvinyl alcohol; and gelatin-based materials. Typically, a combination of one or more of these materials is used to form the absorbent carrier containing the therapeutic agent of the present invention. After applying a thin film of the composition to the skin as a mask, the film is allowed to dry for a period of time (typically 20 minutes). The absorbent carrier will absorb skin oils during the drying process, thus degreasing the skin. The acidic treatment material will be slowly released onto the degreased skin as the composition dries and remains on the skin. At the end of the treatment, the dried film is removed from the skin by rinsing off with water.

In a particularly preferred embodiment of the present invention, the compositions may further comprise from 0.1 to 2% of a limonene-based oil such as lemon oil. As explained in my copending U.S. patent application Ser. No. 08/064,915, filed May 24, 1993, the addition of the limonene-based oil helps to counter the irritating effects encountered in the use of acid containing skin preparations. Unlike prior art attempts to neutralize the highly acidic compositions, the limonene-based oils do not impede the effectiveness of the treatment material.

DETAILED DESCRIPTION OF THE INVENTION

The compositions of the present invention comprise a pharmaceutically and cosmetically acceptable formulations in which up to 20% by volume of an acid material selected from the group consisting of alphahydroxy acids, carboxylic acids, halo-carboxylic acids, dicarboxylic acids, and combinations thereof is combined with up to 40% of an absorbent carrier and sufficient water so that the formulations may be used as a facial mask for the treatment of dry skin, photo-aging, acne, and other skin conditions. Of course, while the term "facial mask" is used, the compositions of the present invention may be used on the skin of any part of the body which requires such treatment, such as for example, the hands.

In addition to the acidic material, absorbent carrier and water, the compositions of the present invention may also include a limonene-based oil selected from the group consisting of lemon oil, orange oil, grapefruit oil, lime oil, bergamot oil, caraway oil, dill oil and combinations thereof. When present, the limonene-based oil comprises up to 2% by volume of the composition. The compositions may further include other substances; for example, if they are to be used for the treatment of dry skin, it is particularly desirable that the compositions include a humectant such as propylene glycol or glycerin. A quantity of coloring agent, such as titanium dioxide, may be present to give the composition a pleasing color. Furthermore, a preservative such as methyl ethyl, or propylparaben will typically be included. Also, in addition to the water described above, the compositions may further comprise a non-aqueous solvent, typically an alcohol such as isopropyl or SDA-40 alcohol. Of course, other ingredients, such as perfumes may be incorporated into the compositions claimed herein.

In a particularly preferred embodiment of the present invention, the acidic material comprises glycolic acid, and the limonene-based oil comprises lemon oil. Preferably, the glycolic acid comprises from between 5 to 10% of the volume of the composition, and the lemon oil comprises between 0.1 to 0.2% of the volume of the composition.

In formulating the compositions of the present invention, the acidic materials such as glycolic acid and the limonene-based oil such as lemon oil may be premixed, either at room temperature or with heating to provide a homogeneous mixture of the acid and the oil. This mixture is then combined with a master mask blend which includes the various components of the absorbent material, the water, and the remaining ingredients, if present. In accordance with procedures known in the prior art, the master mask blend may be first formulated, then dried, ground, and mixed with water to form an ultra fine blend. See, for example, U.S. Pat. No. 4,640,932. The master mask blend is then mixed with the cooled mixture of acid and oil to form the composition of the present invention. Alternatively, the acid and oil may be directly mixed into the mask blend when it is formulated.

The quantity of active compound in a unit dose of the claimed compositions may be varied or adjusted according to the particular application.

Preferably, the compositions of the present invention are most efficacious when used in a routine regimen of skin care, either daily or as directed by a physician. The affected area of the skin is first washed with a mild cleanser, rinsed and patted dry. A thin film of the claimed composition is then applied evenly over the affected area using a circular motion. The film is allowed to dry for 15–30 minutes, during which time the therapeutic agent is slowly released from the mask onto the affected area, thus providing a time release delivery system. The area is then rinsed thoroughly with warm water to remove all of the material and patted dry.

The foregoing description includes reference to certain embodiments and exemplifications of the compositions and method of the present invention. Other variations may occur to one skilled in the art by using the teachings gleaned from the present disclosure. However, such variations are considered to be within the scope of the present invention. The invention is not limited to the exact embodiments and exemplifications described but, rather, to the claims appended hereto and all reasonable equivalents thereof.

I claim:

1. A method of treating skin comprising the steps of:
   I. forming an aqueous mixture consisting essentially of:
      one or more carboxylic acids in an amount greater than zero and up to 20% by volume, each carboxylic acid having at least one substituent selected from the group consisting of: an alphahydroxyl group, a halogen atom and another carboxyl group;
      0.1–2% by volume of a limonene-based oil; and
      a skin oil absorbent carrier in an amount greater than zero and up to 40% by volume said skin oil absorbent carrier including a mineral based material selected from the group consisting of kaolin, magnesium aluminum silicate, bentonite and combinations thereof; and
      the remainder, water;
   II. applying a thin film of said aqueous mixture to the skin of a user;
   III. allowing the film to dry on the skin; and
   IV. removing the dried film with water.

2. The method of claim 1, wherein the carboxylic acid is glycolic acid and the limonene-based oil is lemon oil.

3. A method as in claim 1, wherein said absorbent carrier comprises bentonite and said carboxylic acid comprising trichloroacetic acid.

4. A combination for the treatment of skin consisting essentially of:
   one or more carboxylic acids in an amount greater than zero and up to 20% by volume, each carboxylic acid having at least one substituent selected from the group consisting of: an alphahydroxyl group, a halogen atom and another carboxyl group;
   an amount greater than zero and up to 2% by volume of a limonene-based oil;
   an amount greater than zero and up to 40% by volume of a skin oil absorbent carrier, said skin oil absorbent carrier including a mineral based material selected from the group consisting of kaolin, magnesium aluminum silicate, bentonite and combinations thereof; and
   the remainder, water.

5. The composition of claim 4 wherein the limonene-based oil is selected from the group consisting of: lemon oil, orange oil, grapefruit oil, lime oil, bergamot oil, caraway oil, dill oil and combinations thereof.

6. The composition of claim 4 wherein the carboxylic acid is selected from the group consisting of glycolic acid, trichloroacetic acid, and combinations thereof.

7. The composition of claim 4 wherein the carboxylic acid comprises glycolic acid and the limonene-based oil comprises lemon oil.

8. The composition of claim 4 further comprising a humectant selected from the group consisting of polypropylene glycol and glycerin.

9. The composition of claim 4 further comprising a non-aqueous solvent selected from the group consisting of isopropyl alcohol and SDA-40 alcohol.

10. The composition of claim 4 further comprising a preservative selected from the group consisting of methylparaben, ethylparaben, and propylparaben.

11. A composition as in claim 4, wherein said absorbent carrier comprises bentonite.

12. A composition as in claim 4 wherein said carboxylic acid is trichloroacetic acid.

13. A face mask composition for treating skin conditions such as dry skin, photo-aging, acne or pseudo folliculitis barbae, consisting essentially of, by volume:
   an amount greater than zero and up to 20% by volume of a carboxylic acid selected from the group consisting of glycolic acid, trichloroacetic acid and combinations thereof;
   an amount greater than zero and up to 2% by volume of a limonene-based oil;
   a skin oil amount greater than zero and up to 50% by volume of an absorbent carrier comprising bentonite; and
   the remainder, water.

* * * * *